(12) United States Patent
Ahn et al.

(10) Patent No.: US 7,524,464 B2
(45) Date of Patent: Apr. 28, 2009

(54) SMART DISPOSABLE PLASTIC LAB-ON-A-CHIP FOR POINT-OF-CARE TESTING

(76) Inventors: Chong H. Ahn, 8507 C Apricorn Dr., Cincinnati, OH (US) 45249; Jin-Woo Choi, 10803 Woodland Oaks Dr., Baton Rouge, LA (US) 70809; Gregory Beaucage, 10730 Deerfield Rd., Cincinnati, OH (US) 45242; Joseph Nevin, 6921 Greenfield Dr., Cincinnati, OH (US) 45224

( * ) Notice: Subject to any disclaimer, the term of this patent is extended or adjusted under 35 U.S.C. 154(b) by 616 days.

(21) Appl. No.: 10/947,577

(22) Filed: Sep. 22, 2004

(65) Prior Publication Data
US 2005/0130292 A1 Jun. 16, 2005

Related U.S. Application Data

(60) Provisional application No. 60/506,641, filed on Sep. 26, 2003, provisional application No. 60/506,635, filed on Sep. 26, 2003, provisional application No. 60/506,321, filed on Sep. 26, 2003, provisional application No. 60/506,226, filed on Sep. 26, 2003, provisional application No. 60/506,424, filed on Sep. 26, 2003.

(51) Int. Cl.
C12M 1/68 (2006.01)
C12M 1/34 (2006.01)
H01L 21/00 (2006.01)
(52) U.S. Cl. ............... 422/177; 435/283.1; 435/287.1; 435/287.8; 435/288.4; 435/288.5; 422/168
(58) Field of Classification Search .................. 422/177; 73/1.02
See application file for complete search history.

(56) References Cited

U.S. PATENT DOCUMENTS 5,405,510 A 4/1995 Betts et al.

(Continued)

FOREIGN PATENT DOCUMENTS

EP 1 245 279 10/2002

(Continued)

OTHER PUBLICATIONS

Gao et al, A fully integrated biosensor arry for measurement metabolic parameters in human blood, May 2002, 2nd Annual International IEEE-EMBS Special Topic Conference on Microtechnologies in Medicine & Biology, 223-226.*

(Continued)

*Primary Examiner*—Walter D Griffin
*Assistant Examiner*—Christine T Mui
(74) *Attorney, Agent, or Firm*—Joseph F. Aceto, Esq.; James L. Wilcox, Esq.

(57) ABSTRACT

Disclosed herein is a fully-integrated, disposable biochip for point-of-care testing of clinically relevant parameters. Specifically, in accordance with an embodiment of the present invention, the biochip is designed for POCT (point-of-care-testing) of an array of metabolic parameters including partial pressure of oxygen, Glucose, and Lactate concentration from venous blood samples. The biochip is fabricated on a low-cost plastic substrate using mass manufacturing compatible fabrication processes. Furthermore, the biochip contains a fully-integrated metallic micro-needle for blood sampling. The biochip also uses smart passive microfluidics in conjunction with low-power functional on-chip pressure generators for microfluidic sequencing. The design, configuration, assembly and operation of the biochip are ideally suited for a disposable biochip specifically targeted towards POCT applications.

14 Claims, 13 Drawing Sheets

U.S. PATENT DOCUMENTS

| | | | |
|---|---|---|---|
| 5,660,993 | A | 8/1997 | Cathey et al. |
| 5,747,666 | A * | 5/1998 | Willis .......................... 73/1.02 |
| 5,837,454 | A | 11/1998 | Cozzette et al. |
| 6,306,594 | B1 | 10/2001 | Cozzette et al. |
| 6,479,727 | B1 | 11/2002 | Roe |
| 6,537,501 | B1 | 3/2003 | Holl et al. |
| 6,773,671 | B1 | 8/2004 | Lewis et al. |
| 2002/0155586 | A1 | 10/2002 | Cheng et al. |
| 2003/0186228 | A1 | 10/2003 | McDevitt et al. |
| 2004/0115094 | A1 | 6/2004 | Gumbrecht et al. |

FOREIGN PATENT DOCUMENTS

| | | |
|---|---|---|
| EP | 1 245 943 | 10/2002 |
| WO | WO 99/33559 | 7/1999 |
| WO | WO 99/60397 | 11/1999 |
| WO | WO 00/21659 | 4/2000 |
| WO | WO 03/080868 | 10/2003 |
| WO | WO 03/091731 | 11/2003 |

OTHER PUBLICATIONS

Tortella et al, Precision, Accuracy, and Managed Care Implications of a Hand-Held Whole Blood Analyzer in the Prehospital Setting, Jul. 1996, American Journal of Clinical Pathology, vol. 106, No. 1, 124-127.*

Kopf-Sill, Anne R., Successes and challenges of lab-on-a-chip, Lab Chip, 2002, 2, 42N-47N.*

Gawad, S. et al, Micromachined impedance spectroscopy flow cytometer for cell analysis and particle sizing, 2001, Lab on a Chip, 1, 76-82.*

Walker et al, A passive pumping method for microfluidic devices, 2002, Lab on a Chip, 2, 131-134.*

Papadea C et al, Evaluation of the i-STAT Portable Clinical Analyzer for Point-of-Care Blood Testing in the Intensive Care Units of a University Children's Hospital, 2002, Alans of Clinical & Laboratory Science, 32, 3, 231-243.*

Ahn, et al, "Disposable Smart Lab-On-A-Chip For Point-Of-Care Clinical Diagnostics (Invited Paper)," Proceedings of the IEEE, Special Issue on Biomedical Applications for MEMS and Microfluidics, 2004, p. 154-173.

Puntambekar, et al, "Smark Disposable Plastic Lab-On-A-Chip For Point-Of-Car Testing (POCT)," Proceedings of the 7th International Conference on Micro TOtal Analysis SYstems (micro-TAS 2003), p. 1291-1294.

Choi, et al, "A Disposable Plastic Biochip Cartridge With On-Chip Power Sources For BLood Analysis," Proceedings of the 16th IEEE MEMS WOrkship (MEMS '03), p. 447-450.

Ahn, et al, "Disposable Biochip Cartridge for Clinical Diagnostics Toward Point-Of-Care Systems," Proceedings of the 6th International Conference on Micro Total Analysis Systems (micro-TAS 2002), p. 187-189.

Ahn, et al, "Disposable Smart Plastic Biochips for Clinical Diagnostics," BioMEMS Conference, Material Research Society (MRS).

Choi, et al, "A Plastic Micro Injection Molding Technique Using Replaceable Mold-Disks For Disposable Microfluidic Systems and Biochips," Proceedings of the 5th International Conference on Micro Total Analysis Systems (micro-TAS 2001), p. 411-412.

Han, et al, "UV Adhesive Bonding Techniques In Room Temperature For Plastic Lab-On-A-Chips," Proceedings of the 7th International Conference on Micro Total Analysis Systems (micro-TAS 2003), p. 599-602.

Putambeker, et al, "Integration Of Metallic Microneedles With Disposable Biochips for Minimally Invasive Blood Sampling," Proceedings of the 7th International Conference on Micro Total Analysis Systems (micro-TAS 2003), p. 599-602.

Puntambekar, et al, "Fixed-Volume Metering Microdispenser Module," Lab On A Chip, The Royal Society of Chemistry 2002, vol. 2 (No. 4), p. 213-218.

Puntambeker, et al, "An Air-Driven Fluidic Multiplexer Intefrated with Microdispensers," Proceedings of the 5th International Conference on Micro Total Analysis Systems (micro-TAS 2001) (Monterey, CA, Oct. 21-25, 2001), p. 78-80.

Hong, et al, "A Functional On-Chip Pressure Generator Using Solid Chemical Propellant for Disposable Lab-On-A-Chip," Lab-On-A-Chip, The Royal Society of Chemistry 2003, p. 281-286.

Hong, et al, "A Functional On-Chip Pressure Generator Using Solid Chemical Propellant For Disposable Lab-On-A-Chip," Proceedings of the 16th IEEE MEMS Workshop (MEMS '03), p. 16-19.

Zhu, et al, "Development Of Inexpensive Biosensor Array For Point-Of-Care Testing," Proceedings of the 7th International Conference on Micro Total Analysis Systems (micro-TAS 2003), p. 797-800.

Gao, et al, "A Fully Integrated Biosensor Array for Measurement of Metabolic Parameters in Human Blood," Proceedings of the 2nd Annual International IEEE-EMBS Special Topic Conference on Microtechnologies in Medicine & Biology, p. 223-226.

Gao, et al, "A Novel Glusose Biosensor with Gel-Based Soild Electrolyte and Microheater Structure for Rapid Detection," Proceedings of the 7th World Congress on Biosensors, p. 2-3.68.

* cited by examiner

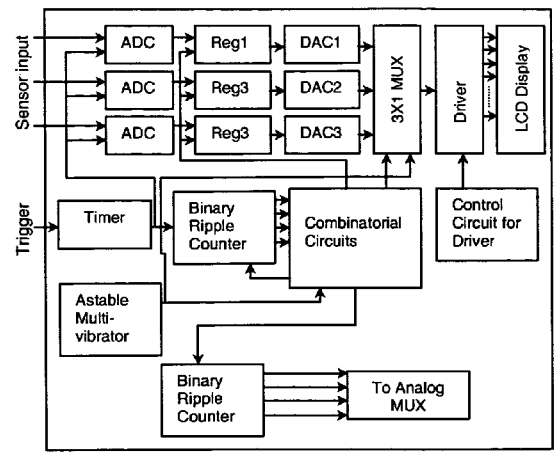
Fig. 6a
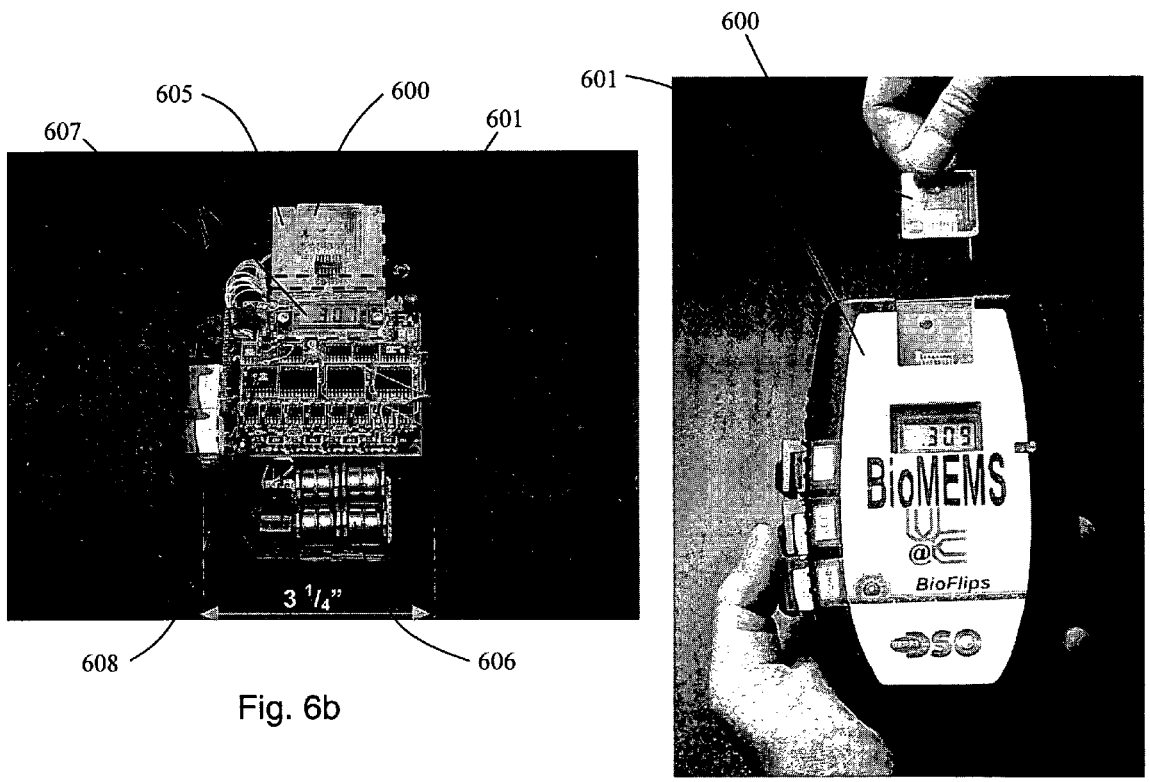
Fig. 6b
Fig. 6c

SMART DISPOSABLE PLASTIC LAB-ON-A-CHIP FOR POINT-OF-CARE TESTING

CROSS-REFERENCE TO RELATED APPLICATIONS/INCORPORATION BY REFERENCE

This application claims priority to provisional U.S. Patent Application Ser. Nos. 60/506,641; 60/506,226; 60/506,321; 60/506,424; and 60/506,635 all filed on Sep. 26, 2003, and all of which are incorporated herein by reference in their entirety.

This patent application is being filed concurrently with U.S. patent application Ser. Nos. 10/946,685, 10/947,576, 10/946,818 and 10/947,557, which are incorporated herein by reference in their entirety.

GOVERNMENT SUPPORT

The U.S. Government has a paid-up license in this invention and the right in limited circumstances to require the patent owner to license others on reasonable terms as provided for by the terms of grant no. AF F30602-00-1-0569 awarded by the Defense Advanced Research Projects Agency (DARPA).

TECHNICAL FIELD

Embodiments of the present invention generally relate to the development of fully-integrated, low cost, plastic based, disposable biochips for clinical diagnostic applications. Described herein is a passive microfluidic control system, an on-chip power source using solid-propellant actuators, an integrated metallic microneedle for sampling, an on-chip calibration pouch for calibration buffer storage, a biosensor array for measuring clinically relevant parameters, a biochip socket for mechanical operations of a biochip sequence, and a handheld analyzer for controlling the microfluidic sequencing of the biochip and reading the output of the biosensors.

BACKGROUND OF THE INVENTION

There is a large demand to develop miniaturized blood analysis systems for rapid and reliable point-of-care testing and monitoring. Such systems would significantly enhance the quality of healthcare by offering immediate measurement of several clinically relevant parameters that can be used to assess a patient's health.

Microfluidic devices fabricated using MEMS technology offer the possibility of delivering such a system. In order to realize disposable biochips (to avoid cross-contamination of samples and measurement errors) it is necessary to have a reliable microfluidic control system that can be implemented on a low-cost substrate. The use of MEMS based devices such as microvalves and micropumps adds to the cost of the system and necessitates the use of complex control systems. Another challenging factor in realizing disposable biochips is a simple yet non-complex actuation source for fluidic driving. Micropumps are typically expensive and also difficult to integrate. The sampling of blood is considered another challenging aspect since most microfabricated needles cannot puncture to sufficient depth for venous blood sampling, which is the most commonly accepted sample source.

Sensitive biosensor arrays are also desired which can reliably measure the clinically relevant parameters at the typical concentrations observed in human blood with adequate accuracy and precision. Furthermore, the sensor array should be fully integrated with the biochip, preferably on the same low-cost substrate as the remaining biochip for ease of integration and low-cost. The developed sensor array should be able to perform well outside laboratory environments where interfering signals such as temperature variations must not affect the sensor performance.

To realize a fully integrated, disposable biochip that can be deployed for point-of-care testing (POCT) applications, a number of criteria have to be met. Based in part on the discussion above, some of these can be listed as: (a) low cost per disposable biochip wherein the low cost necessitates the use of low-cost biocompatible substrate materials; (b) a low cost, mass producible fabrication process for the biochips wherein the high manufacturing volumes reduce the per device cost; (c) fully-integrated sampling capability, the use of which allows for the biochip to directly acquire blood samples; (d) on-chip storage of reagents/buffers such that the biochip is a self-contained unit; (e) integrated biosensor array wherein the biosensor array is fabricated on essentially the same substrate as the rest of the biochip and can be easily integrated with the rest of the biochip; (f) a low-cost, high volume compatible fabrication process for the biosensor array wherein the high volume manufacturing drives down the cost of the each sensor array; (g) a fully integrated pumping modality which can achieve the desired microfluidic sequencing wherein the pumping technique does not involve any moving parts to increase the reliability of operation; (h) the fully integrated pumping modality which requires minimal external power for operation; (i) the pumping modality wherein the micropump can be easily integrated with the biochip and whose operation can be regulated with minimal control signals (j) preferably passive microfluidic control system with no moving parts for flow sequence regulation; (k) the fully integrated biochip wherein minimal control signals are required to initiate and maintain microfluidic sequencing and interrogate the biosensor arrays; and (l) a suitable analyzer module (handheld or smaller) which can be used to regulate operation of the biochip.

To date, a number of inventions have described a so-called "integrated biochip" or "disposable biochip". For example, WO9960397A1, incorporated in its entirety by reference herein, describes a liquid analysis cartridge wherein the cartridge is fabricated on a low-cost substrate using lamination techniques and incorporates most of the requirements listed above with the notable exception of an on-chip pumping source. WO0021659A1, incorporated herein in its entirety by reference, describes yet another microfluidic device wherein the device is manufactured using a specialized ceramic substrate and incorporates only the microfluidic components described above. Furthermore, this device also uses active power-hungry components thereby rendering it less than ideal for POCT applications. WO9933559A1, incorporated herein in its entirety by reference, describes a fairly complex microfluidic device that relies on re-constitution of on-chip stored reagents and also has on-chip reaction chambers for biochemical reactions. This system too, does not have on-chip pumping sources. U.S. Pat. No. 566,093, incorporated herein in its entirety by reference, describes a "Disposable device in Diagnostic Assays" wherein passive capillary fluidic driving and valving is used for flow regulation. This system is more suited for POCT applications, although it does not contain any integrated sampling scheme. Other examples of diagnostics microfluidic devices are presented in U.S. Pat. No. 6,537,501, US2002015586A1, U.S. Pat. No. 647,927, U.S. Pat. No. 5,405,510, US20040115094A1, U.S. Pat. No. 6,773,671, and US20030186228A1, all incorporated herein in their entirety by reference. An interesting microfluidic device which uses centrifugal forces (generated by a spinning motion imparted to the substrate) is disclosed in WO03080868A1, incorporated herein in its entirety by reference. All these system suffer from a couple of notable drawbacks namely; the lack of an efficient, low-power consumption pumping arrangement and lack of an integrated sampling arrangement. EP1245943A2, incorporated herein in its entirety by reference, describes a system for collecting whole blood for analysis by a microfluidic system and as clearly illustrated herein, the device is fairly complex with a filtering scheme together with the sampling canula. EP1245279A2, incorporated herein in its entirety by reference, illustrates the most commonly used approach for delivering samples to the microfluidic system, wherein the sample is first collected using a conventional syringe and subsequently transferred to the microdevice using an appropriate interface. This inhibits the widespread use of the microfluidic devices, partly due to the need for an extra sampling and also because this method employs a conventional needle, which is relatively painful when compared with microneedles. However, as mentioned previously, most microneedles fabricated using MEMS techniques are not suitable for venous sampling due to the either dimensional or structural integrity concerns.

A notable exception is the handheld analysis system developed by the I-STAT® Corporation which also uses a disposable analysis cartridge. The cartridge is not manufactured using conventional MEMS based processes but the dimensions are fairly small compared to the conventional analysis equipment thereby making it a potentially viable candidate for competing in the POCT area. The biosensors for the aforementioned analysis cartridge are manufactured on a Silicon substrate whereas the bulk of the cartridge itself is manufactured from. plastics as illustrated in U.S. Pat. No. 5,837,454 and U.S. Pat. No. 6,306,594, incorporated herein in their entirety by reference. Coupled with the high intrinsic cost of the Silicon substrate, the complex, time-consuming assembly for dissimilar substrates further adds to the cost of the device. Also, this device uses an external motor to actuate a plunger which subsequently causes fluidic displacement. Consequently, the energy demand for operating this cartridge is fairly high. Finally, this device too requires sample injection from a syringe wherein the blood has been previously collected.

SUMMARY OF THE INVENTION

Certain embodiments of the present invention provide a low-cost, disposable biochip that addresses the above listed problems and can be successfully applied for the measurement of clinically relevant parameters from human blood. A fully-integrated disposable biochip ideally suited towards POCT analysis of clinically relevant parameters is disclosed. In accordance with an embodiment of the present invention, the disposable biochip can be used for simultaneous detection of multiple metabolic parameters such as $PO_2$ (partial pressure of oxygen), glucose and lactate, although in principle the applications of the biochip can be extended to a variety of other analytes.

In accordance with an embodiment of the present invention, the disposable biochip is composed of four (4) layers of plastic substrates assembled together using a combination of thermoplastic fusion bonding, room-temperature UV-adhesive bonding, and adhesive bonding. The microfluidic system is designed to sample a specific volume of sample via the integrated microneedle and store it in a sampling channel. The biochip also contains an on-chip calibration buffer pouch. The calibration buffer is used to calibrate the sensor performance at the given environmental conditions. Following this, the on-chip functional pressure generator is actuated to deliver a known volume of the sample to the sensing reservoir, which houses the biosensor array, for measurement of clinically relevant parameters.

The disposable biochip contains an integrated microneedle that allows for a fully-integrated sampling scheme while minimizing the pain due to its minimally invasive nature. In accordance with an embodiment of the present invention, a conventional metallic microneedle is integrated with the biochip during biochip assembly.

An embodiment of a disposable biochip disclosed herein relies on two fluidic driving mechanisms both of which use minimal or no external power and are ideally suited for a POCT biochip. In a first case, the mechanical motion of the custom designed socket (in which the biochip is inserted after sampling) forces flow of the calibration buffer. For this sequencing, the energy used for microfluidic flow is transferred by the motion imparted to the socket by the user and does not require any additional power from the analyzer and/or the biochip. In the next step, when the on-chip collected sample solution is to be delivered, a functional pressure generator of the type disclosed in U.S. patent application Ser. No. 09/946,818 and which is incorporated herein in its entirety by reference, is actuated which ensures precise fluidic displacement with minimal power consumption.

Furthermore, in such an embodiment of a biochip design, the biosensor array is fabricated as a fully integrated portion of the biochip on the same substrate material as the remainder of the biochip. Also, the biosensor array is fabricated using a low cost, high volume fabrication technique wherein an array of sensor materials may be deposited simultaneously thereby reducing the fabrication/assembly costs.

Without intent of limiting the scope of application of the present invention, the application of the present invention is generally a low-cost, disposable plastic biochip for point-of-care testing of clinically relevant metabolic parameters.

Certain aspects of the biochip fabrication and operation are presented in Ahn et al, Proceedings of the IEEE, Special Issue on Biomedical Applications for MEMS and Microfluidics, Vol. 92, pp. 154-173, 2004; Puntambekar et al, Proceedings of the 7th International Conference on Micro Total Analysis Systems (micro-TAS 2003), California, USA, Oct. 5-9, 2003, pp. 1291-1294; Choi et al, Proceedings of the 16th IEEE MEMS Workshop (MEMS '03), Kyoto, Japan, Jan. 19-23, 2003, pp. 447-450; Ahn et al, Proceedings of the 6th International Conference on Micro Total Analysis Systems (micro-TAS 2002), Nara, Japan, Nov. 3-7, 2002, pp. 187-189; and Ahn et al, BioMEMS Conference, Material Research Society (MRS), San Francisco, Apr. 1-3, 2002.

Certain aspects of the plastic fabrication processes and the material aspects are described in detail in Choi et al, Proceedings of the 5th International Conference on Micro Total Analysis Systems (micro-TAS 2001), Monterey, Calif., Oct. 21-25, 2001, pp. 411-412 and Han et al, Proceedings of the 7th International Conference on Micro Total Analysis Systems (micro-TAS 2003), California, USA, Oct. 5-9, 2003, pp. 1113-1116 and as disclosed in U.S. patent application Ser. No. 10/947,557 which is incorporated herein in its entirety by reference.

The metallic microneedle integration and operation, as a part of the biochip, is described in Puntambekar et al, Proceedings of the 7th International Conference on Micro Total Analysis Systems (micro-TAS 2003), California, USA, Oct. 5-9, 2003, p. 599-602.

Puntambekar et al, Lab on a Chip, Vol. 2, Issue 4, pp. 213-218, 2002 and Puntambekar et al, Proceedings of the 5th International Conference on Micro Total Analysis Systems (micro-TAS 2001), Monterey, Calif., Oct. 21-25, 2001, pp. 78-80 describe in detail certain aspects of the smart, passive microfluidic system concepts that are employed for developing the biochip described herein. Note that the smart microfluidics, or sPROMs concepts, are originally disclosed in U.S. Provisional Patent Application Ser. Nos. 60/204,214 filed on May 12, 2000 and 60/209,051 filed on Jun. 2, 2000, and U.S. patent application Ser. No. 10/602,575 filed on Jun. 24, 2003 and which are incorporated herein in their entirety by reference.

The principles and operation of the functional on-chip pressure source is described in Hong et al, Lab. Chip., 3, pp. 281-286, 2003 and Hong et al, Proceedings of the 16th IEEE MEMS Workshop (MEMS '03), Kyoto, Japan, Jan. 19-23, 2003, pp. 16-19, and also disclosed in U.S. patent application Ser. No. 10/946,818, incorporated herein in its entirety by reference.

Finally Gao et al, Proceedings of the 7th International Conference on Micro Total Analysis Systems (micro-TAS 2003), California, USA, Oct. 5-9, 2003, pp. 797-800; Gao et al, Proceedings of the 2nd Second Annual International IEEE-EMBS Special Topic Conference on Microtechnologies in Medicine & Biology, Madison, Wis., May 2-4, 2002, pp. 223-226; and Gao et al, Proceedings of the 7th World Congress on Biosensors, Kyoto, Japan, May 15-17, 2002, P2-3.68, describe certain aspects of the biosensor array of the biochip, including certain details on the principles of operation, fabrication and integration with the biochip.

As is abundantly clear from the preceding discussion, the present invention seeks to address the deficiencies and inadequacies in the prior art as described in the previous section and as generally known in the industry.

Certain embodiments of the present invention provide for the development of a fully-integrated, disposable biochip suitable for POCT analysis of multiple clinically relevant parameters.

Certain embodiments of the present invention provide for the development of a low cost biochip using plastic substrates and/or mass production manufacturing practices.

Certain embodiments of the present invention provide for the development of a disposable biochip with an integrated microneedle for minimally invasive sampling in an on-chip integrated format.

Certain embodiments of the present invention provide for the development of a disposable biochip with smart, programmable passive microfluidics for flow sequencing wherein no active flow regulation components are required.

Certain embodiments of the present invention provide for the development of a disposable biochip with an easy to control, low power consuming and functional pressure control source which is easily integrated with the biochip.

Certain embodiments of the present invention provide for the development of low cost manufacturing practices for fabrication of biosensor arrays to be integrated with the biochip.

Other embodiments, features and advantages of the present invention will become apparent from the detailed description of various embodiments of the present invention when considered in conjunction with the accompanying drawings.

BRIEF DESCRIPTION OF THE DRAWINGS

The present invention, as defined in the claims, can be better understood with reference to the following drawings and microphotographs of the actual devices. The drawings are not all necessarily drawn to scale, emphasis instead being placed upon clearly illustrating principles of the present invention.

FIGS. 6a-6c show a handheld analyzer used in conjunction with a biochip for detection of clinically relevant metabolic parameters, in accordance with an embodiment of the present invention.

DETAILED DESCRIPTION OF THE INVENTION

Figure 1A:
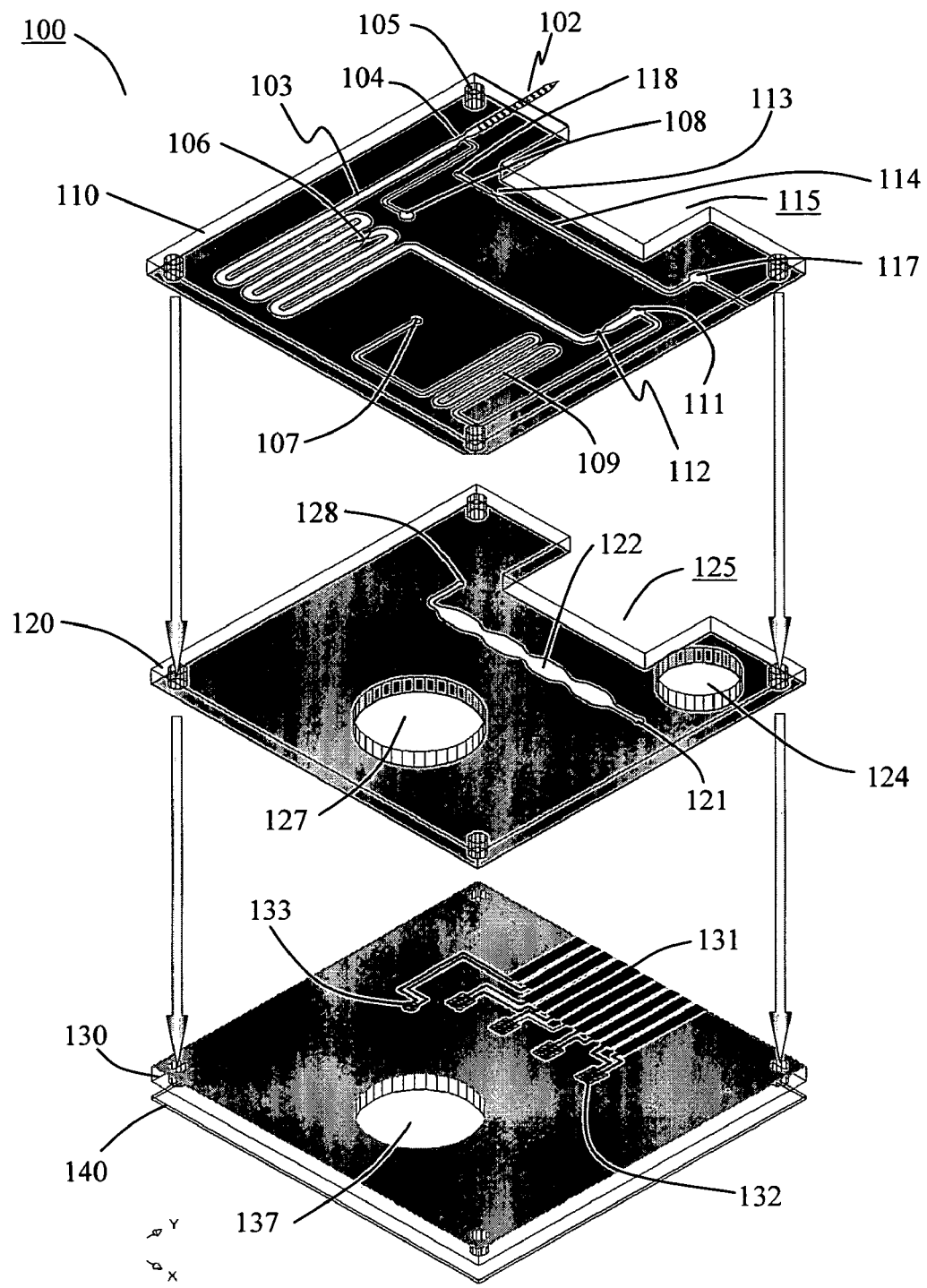
FIGS. 1a-1b are a schematic illustration of a multi-layer biochip and a microphotograph showing the actual fabricated and assembled biochip, in accordance with an embodiment of the present invention.

Certain embodiments of the present invention include, generally stated, a fully-integrated disposable biochip for point-of-care testing of clinically relevant metabolic parameters. Disclosed herein are a number of novel features for the disposable biochip such as the integrated microneedle, on-chip functional pressure source, biosensor array, and smart passive microfluidics.

Definitions

The process of "Microfabrication", as described herein, relates to the process used for manufacture of micrometer sized features on a variety of substrates using standard microfabrication techniques as understood widely by those skilled in the art. The process of microfabrication typically involves a combination of processes such as photolithography, wet etching, dry etching, electroplating, laser ablation, chemical deposition, plasma deposition, surface modification, injection molding, hot embossing, thermoplastic fusion bonding, low temperature bonding using adhesives, and other processes commonly used for manufacture of MEMS (microelectromechanical systems) or semiconductor devices. "Microfabricated" or "microfabricated devices" as used herein refers to the patterns or devices manufactured using the microfabrication technology.

The term "BioMEMS" as used herein describes devices fabricated using MEMS techniques specifically applied towards biochemical applications. Such applications may include detection, sample preparation, purification, isolation etc. and are generally well know to those skilled in the art. One such technique that is commonly used in BioMEMS applications is that of "Capillary Electrophoresis" (CE). CE refers to the process wherein an electrical field is applied across a liquid column leading to the separation of its constituents based on their mass/charge ratio. The term "CE Chips" refers to microfluidic BioMEMS devices specifically used for CE applications.

The term "chip", "microchip", or "microfluidic chip" as used herein means a microfluidic device generally containing a multitude of microchannels and chambers that may or may not be interconnected with each another. Typically, such biochips include a multitude of active or passive components such as microchannels, microvalves, micropumps, biosensors, ports, flow conduits, filters, fluidic interconnections, electrical interconnects, microelectrodes, and related control systems. More specifically the term "biochip" is used to define a chip that is used for detection of biochemically relevant parameters from a liquid or gaseous sample. The microfluidic system of the biochip regulates the motion of the liquids or gases on the biochip and generally provides flow control with the aim of interaction with the analytical components, such as biosensors, for analysis of the required parameter.

The term "microchannel" as used herein refers to a groove or plurality of grooves created on a suitable substrate with at least one of the dimensions of the groove being in the micrometer range. Microchannels may have widths, lengths, and/or depths ranging from 1 µm to 1000 µm. It should be noted that the terms "channel" and "microchannel" are used interchangeably in this description. Microchannels can be used as stand-alone units or in conjunction with other microchannels to form a network of channels with a plurality of flow paths and intersections.

The term "microfluidic" generally refers to the use of microchannels for transport of liquids or gases. The microfluidic system consists of a multitude of microchannels forming a network and associated flow control components such as pumps, valves and filters. Microfluidic systems are ideally suited for controlling minute volumes of liquids or gases. Typically, microfluidic systems can be designed to handle fluid volumes ranging from the picoliter to the milliliter range.

The term "substrate" as used herein refers to the structural component used for fabrication of the micrometer sized features using microfabrication techniques. A wide variety of substrate materials are commonly used for microfabrication including, but not limited to silicon, glass, polymers, plastics, and ceramics to name a few. The substrate material may be transparent or opaque, dimensionally rigid, semi-rigid or flexible, as per the application they are used for. Generally, microfluidic devices comprise at least two substrate layers where one of the faces of one substrate layer contains the microchannels and one face of the second substrate layer is used to seal the microchannels. The terms "substrate" and "layer" are used interchangeably in this description. Specifically, the substrate is a material that can withstand the thermal dissociation temperature of the solid-propellant materials.

The term "UV-LIGA" describes a photolithography process modeled on the "LIGA" fabrication approach. LIGA refers to the microfabrication process for creating microstructures with high aspect ratio using synchrotron radiation and thick photoresists (ranging in film thickness from 1 µm to 5 mm). The LIGA process is used to form a template that can be used directly or further processed using techniques such as electroplating to create the microfluidic template. UV-LIGA uses modified photoresists that can be spin coated in thicknesses of 1 µm to 1 mm and are sensitive to UV radiation. UV radiation sources are commonly used in microfabrication facilities and hence UV-LIGA offers a lower cost alternative to LIGA for fabrication of high aspect ratio microstructures.

The term "master mold" as used herein refers to a replication template, typically manufactured on a metallic or Silicon substrate. The features of the master mold are fabricated using the UV-LIGA and other microfabrication processes. The microstructures created on the master mold may be of the same material as the master mold substrate e.g. Nickel microstructures on a Nickel substrate or may be a dissimilar material e.g. photoresist on a Silicon surface. The master mold is typically used for creating microfluidic patterns on a polymer substrate using techniques such as hot embossing, injection molding, and casting.

The term "bonding" as used herein refers to the process of joining at least two substrates, at least one of which has microfabricated structures, e.g. a microchannel, on its surface to form a robust bond between the two substrates such that any liquid introduced in the microchannel is confined within the channel structure. A variety of techniques may be used to bond the two substrates including thermoplastic fusion bonding, liquid adhesive assisted bonding, use of interfacial tape layers, etc. Specifically, in this description, the terms "bonding" and "thermoplastic fusion bonding" are used interchangeably. Thermoplastic fusion bonding involves heating the two substrates to be joined to their glass transition temperature and applying pressure on the two substrates to force them into intimate contact and cause bond formation. Another bonding process, namely the use of UV-adhesive assisted low temperature bonding, is also described herein and is specifically and completely referred to in all occurrences.

The term "microheater", "heater", "igniter" and "micro-igniter" as used herein, refers to a microfabricated heater pattern which is created by depositing a metal layer on a suitable substrate and using microfabrication techniques to define a continuous metal track of precise dimensions from the deposited metal layer. The metal track serves as a resistive heater wherein the passage of current through the metal tracks or electrodes causes a rise in temperature of the metal electrodes due the process of resistive heating. The terms "heater", "microheater", "igniter" and "micro-igniter" are used interchangeably and generally refer to the resistive heater unless specifically described otherwise.

The term "current pulse" or "pulse train" as used herein describes a single pulse or a plurality of precisely defined changes in current over a period of time delivered to the microheater. The current pulse can be created by any electronic controller coupled to a power supply or by designing a specific power supply to deliver the desired current characteristics. Furthermore, a wide variety of current pulses can be created by commonly available controllers such as the square wave pulse, half-square wave pulse, sine wave pulse, half-sine wave pulse, triangular pulse, and half-triangular pulse. Note that generally current pulse refers to a positive as well as negative variation in the magnitude of the current and half pulse refers to only a positive current variation.

The term "solid-propellant" as used herein refers to any material that can liberate a substantial volume of gas upon direct heating. The liberated gas may be biochemically reactive such as Oxygen or a biochemically inert gas such as Nitrogen. A wide variety of solid-propellants are available commonly with varying properties in terms of physical structure i.e. liquid or solid, chemical composition, dissociation temperature, chemical structure of released gas, volume of released gas and so on. The choice of a suitable propellant is governed by a number of factors such as chemical nature of the evolved gas, volume of evolved gas, dissociation temperature, toxicity or lack thereof of the gaseous and non-gaseous components after dissociation. In this description, azobis-isobutyronitrile (AIBN) is described as the solid-propellant, however it is understood that any suitable solid-propellant that matches the characteristics stated above for the given application may be substituted instead of AIBN and the scope of the present invention is not limited to this particular material.

The term "thermal dissociation" as used herein, refers to the chemical breakdown of a solid propellant material specifically after application of heat with concurrent liberation of a substantial volume of a gaseous product. The "dissociation temperature" is generally a range of temperature, rather than a precisely defined temperature, over which the thermal dissociation process occurs. Depending on the material of the solid-propellant the range over which dissociation and gas evolution occurs generally spans a temperature range of approximately 10 to 60° C. beyond a minimum dissociation temperature. Most solid-propellants have a "primary dissociation temperature" and a "secondary dissociation temperature" or "breakdown temperature". The term "dissociation temperature" is generally used to describe the "primary dissociation temperature" in this description. The "secondary dissociation temperature" refers to a range of temperature typically higher than the "primary dissociation temperature" at which the non-gaseous components left behind after primary dissociation are further broken down due to heat. Specifically for this application, heating solid propellants to the "secondary dissociation temperature" is generally undesirable since no additional gas is evolved and more energy is required to reach the secondary dissociation temperature.

The term "matrix" as used herein, describes a material that can physically entrap solid or liquid solid-propellant particles without allowing them to escape freely. Furthermore, the matrix material simultaneously exhibits a high porosity for gaseous components such that the gas evolved after heating the solid-propellant material can easily escape the matrix material. An additional requirement for the matrix material is that it should not be chemically reactive with the solid propellant. Also, the matrix material should be able to retain the desired physical characteristics at the dissociation temperature of the solid-propellant.

The term "micropump" as used herein, refers to a device or arrangement that can provide force for displacement of liquids or gases entrapped within a microchannel. A wide variety of pumping mechanisms are known in the art and specifically in this description the "micropump" is of a positive displacement type wherein the pump generates a positive pressure, above the atmospheric pressure, and the higher pressure is coupled to one of a microfluidic column via suitable fluidic interconnects and microchannels. The differential pressure causes movement of the liquid plug or column. An "integrated micropump" or "integrated pressure source" or "on-chip micropump" or "on-chip pressure source" as used herein, refers to a micropump configuration that is irreversibly attached or is an integral part of the microfluidic chip. The above listed terms are used interchangeably in this description.

The "functional on-chip pressure generator" or "functional pressure generator" or "functional on-chip pressure generator using solid-propellant" as used herein, are used interchangeably, and refer to a positive pressure source whose output, i.e. the pressure, can be dynamically regulated after the pressure source has been fabricated and assembled or integrated with the biochip.

The term "membrane" as used herein refers to components of the on-chip biosensors wherein a film of the material is deposited on the substrate, more preferably on the electrodes of the biosensor, using a variety of techniques as well known in the art such as spin-coating, dip-coating, direct deposition, etc. In accordance with an embodiment of the present invention, the biosensor material is deposited as a membrane using spray-coating techniques. Furthermore, the biosensor structure is composed of multiple membranes or "layers" and these terms are used interchangeably in this description.

The intent of defining the terms stated above is to clarify their use in this description and does not explicitly or implicitly limit the application of the present invention by modifications or variations in perception of the definitions.

Smart, Disposable Lab-on-a-Chip for Point-of-Care Testing (POCT) of clinically relevant parameters The structure and operation of the biochip are described in detail in this section. FIG. 1a shows a schematic view of a multi-layer biochip 100, in accordance with an embodiment of the present invention. As shown in FIG. 1a, the biochip comprises three similar layers and one thinner layer. The three layers are fabricated using injection molding techniques by replicating features from a microfabricated mold master. The last layer is actually a flexible adhesive film whose purpose is to contain the calibration solution pouch as described later. In accordance with certain embodiments of the present invention, the layers comprise plastic substrates made of at least one of cyclic olefin copolymer (COC), polyimide, polymethylmethaacrylate, PDMS, polyethylene, and polycarbonate.

Layer 1 110 of the biochip 100 contains most of the microfluidic structures essential for flow sequencing. Layers 1 110 and 2 120 are assembled using thermoplastic fusion bonding techniques and this allows for complete sealing of all the narrow microfluidic channels. In accordance with an embodiment of the present invention, the width of the flow channels ranges from 50 μm to 1 mm whereas the width of the narrow sections constituting the passive valves ranges from 10 μm to 100 μm. The height of all the microfluidic channels in the biochip ranges from 10 μm to 250 μm. The height of all the microchannels on any one layer is approximately the same whereas the heights of the microchannels on different layers may or may not be the same.

Layer 2 of the biochip contains the detection (or sensing) reservoirs 122 (micro-sensor reservoirs). The calibration buffer solution and subsequently the sample solution are displaced to this reservoir from their original position for detection. The sensing reservoirs are on the opposite face of the biosensor array 132 and hence any liquid entering the sensing layer is in fluidic contact with the sensor array. It is important to ensure that the two layers are well aligned during bonding such that transfer hole pairs 118 and 128 and also 111 and 121 align correctly to minimize any dead volume at the layer transfer region. Layer 2 120 also houses the waste reservoir 124, wherein the used calibration buffer solution is expended after use.

The assembled layers 1 and 2 are then combined with layer 3 130 using UV-adhesive assisted room temperature bonding techniques. This is essential owing to the temperature sensitive materials on Layer 3. Specifically, Layer 3 houses the solid-propellant material required for the on-chip functional pressure source 133 (micro-propulsion system). In the accordance with an embodiment of the present invention, this material is AIBN which has a dissociation temperature of approximately 68° C. Since, in the thermoplastic bonding process, the temperatures associated with the process are approximately 80 to 140° C. it is essential that the solid propellant material not be exposed to temperatures in this range.

In accordance with an alternative embodiment of the present invention, the micro-propulsion system of the biochip may include at least one micro-chamber containing pressurized gas and being connected to a passive micro-fluidic control system. The micro-propulsion system further includes a micro-heater positioned next to and being in contact with a thermo-plastic membrane of the micro-chamber to release the pressurized gas into an air inlet of the passive micro-fluidic control system upon melting of the thermo-plastic membrane by the micro-heater when an electrical pulse is applied to the micro-heater.

Furthermore, as explained later in this description, Layer 3 also houses the biosensor array which is constituted of multiple layers and at least one of the layers of one of the biosensors (micro-sensors) contains an enzyme material. The enzyme material is adversely affected at temperatures beyond approximately 40° C., hence the need for a low temperature bonding process. Both the solid-propellant actuator and the electrochemical biosensors are connected to the "outside world" or the analyzer via metallic electrode tracks 131. In accordance with an embodiment of the present invention, the electrode tracks are directly fabricated on the plastic substrate by depositing a thin layer of metal on the plastic followed by standard photolithography techniques to define the electrode pattern. Following fabrication of the electrode patterns, the solid-propellant material is deposited onto the micro-heater pattern using techniques described in U.S. patent application Ser. No. 10/946,818, which is incorporated herein by reference. The fabrication of the biosensors (i.e., micro-sensors) is explained in greater details in subsequent sections of this description. Furthermore, Layers 2 120 and 3 130 also contain cavities, 127 and 137 respectively, to contain the calibration solution pouch.

Layer 4 140, as described previously is a flexible plastic film with an adhesive backing. In accordance with an embodiment of the present invention, a highly flexible tape material (capable of deformations up to 800% of its original dimensions before tearing) is used. The function of this layer will be apparent from the discussion about the operation of the biochip.

FIG. 1a also shows the metallic micro-needle 102 as a part of the biochip. Essentially, the metallic microneedle is positioned in an appropriately sized microchannel 103 (acting as a micro-dispenser reservoir) during assembly of Layers 1 and 2 and is firmly trapped in the aforementioned microchannel. A detailed description of the assembly sequence of the microneedle is also provided later in this description.

Figure 1B:
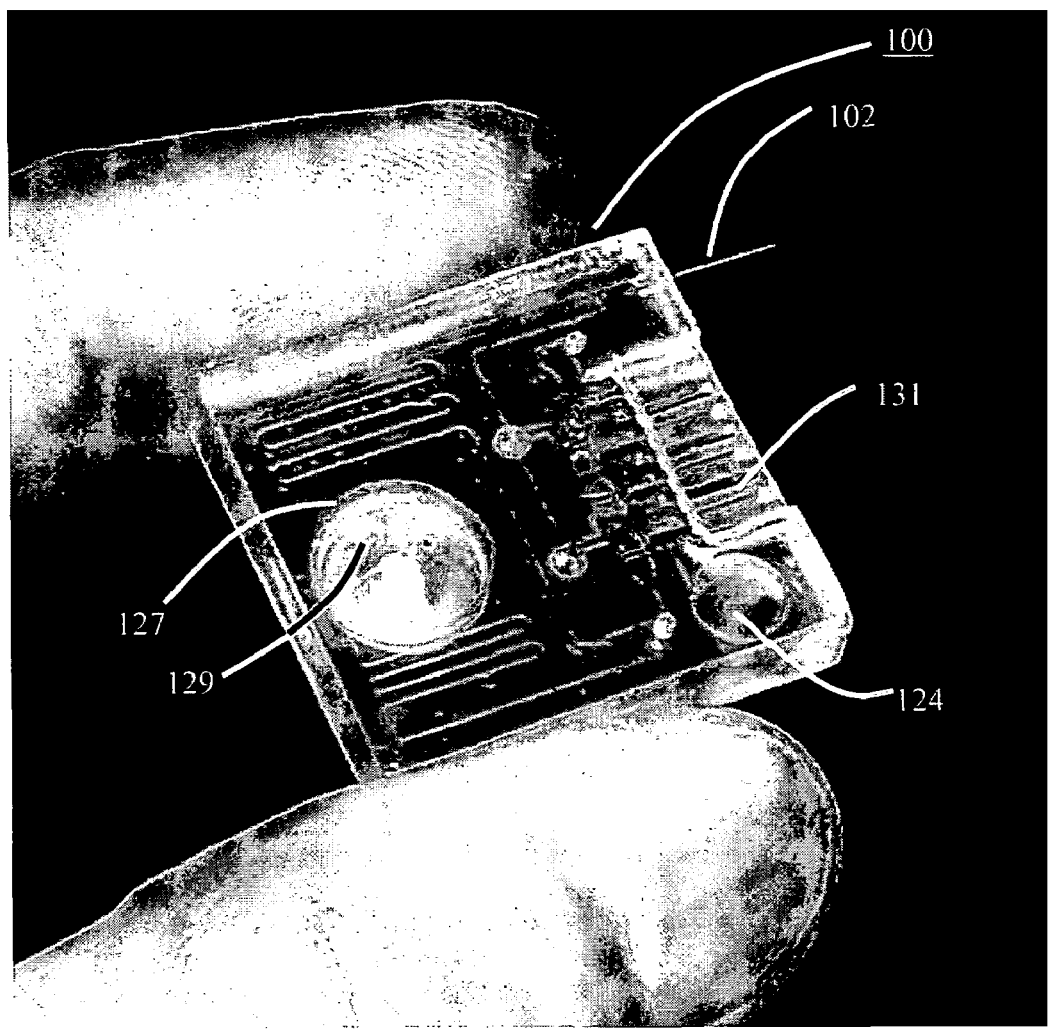

FIG. 1b shows a microphotograph showing the actual fabricated biochip 100. As shown in FIG. 1b, the biochip 100 contains the integrated microneedle 102 as well as the on-chip calibration buffer pouch 129 and the waste reservoir 124 (micro-calibration system). In accordance with an embodiment of the present invention, the dimensions of the biochip 100 are approximately 1"×1"×0.25". To the best of our knowledge, this is currently the smallest biochip with all the functionality incorporated as listed previously.

Figure 2A:
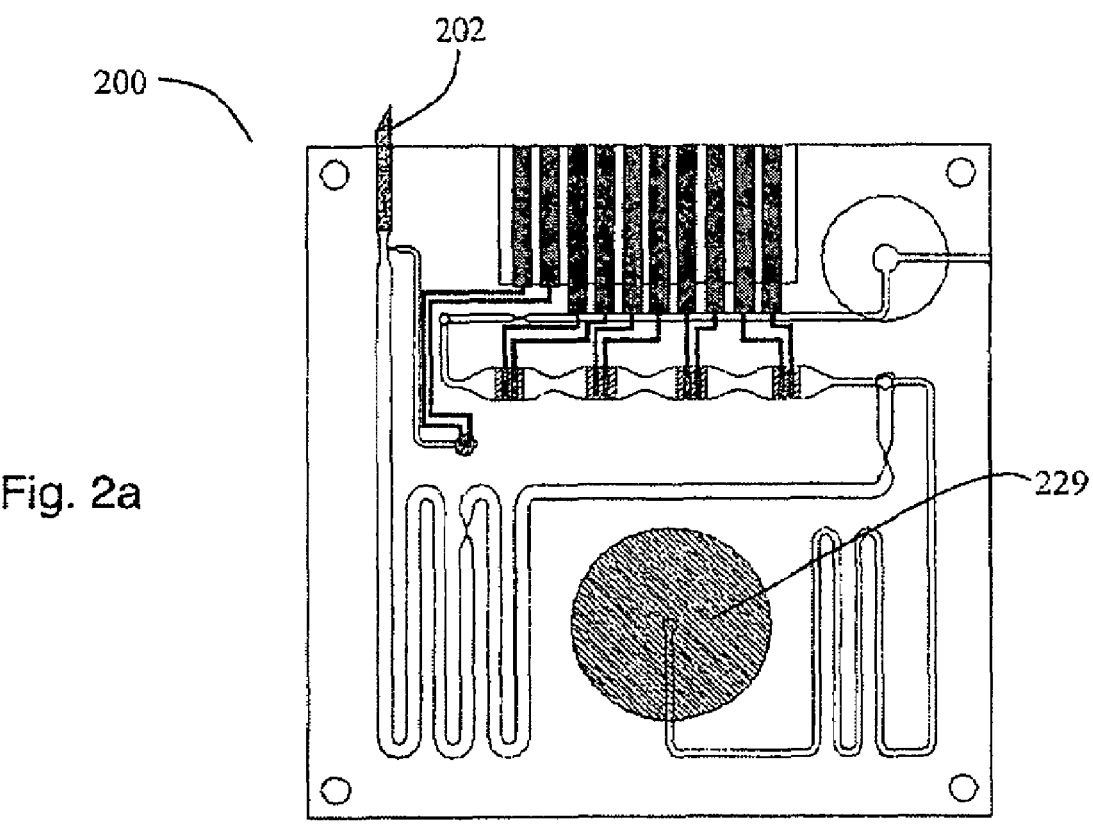
FIGS. 2a-2e show an operational sequence of a biochip, in accordance with an embodiment of the present invention.

FIGS. 2a-2e show the schematic operation sequence of the biochip 200. FIG. 2a shows a plan view of the assembled biochip. As mentioned previously, the micro-needle is positioned between layers 1 and 2 during thermoplastic fusion bonding and integrated during assembly. Furthermore, layer 3 has the biosensor array and the functional on-chip pressure source deposited prior to assembly using room temperature assembly techniques. Following this a metallic pouch 229 containing the calibration solution is assembled into the biochip. A metallic pouch is used for storing the calibration buffer to ensure that there is no gaseous exchange between the calibration solution and the atmosphere thereby adversely affecting the stability of the calibration solution. During assembly, the metallic pouch is positioned within cavities which extend throughout the thickness of layers 2 and 3. Then Layer 4, which is a flexible tape, is pressed against the open surface of Layer 3. The flexible tape layer seals the cavity on Layer 3 such that when the calibration solution pouch is broken, the liquid will enter the microfluidic channels 209 of the biochip 200 on Layer 1.

Figure 2B:
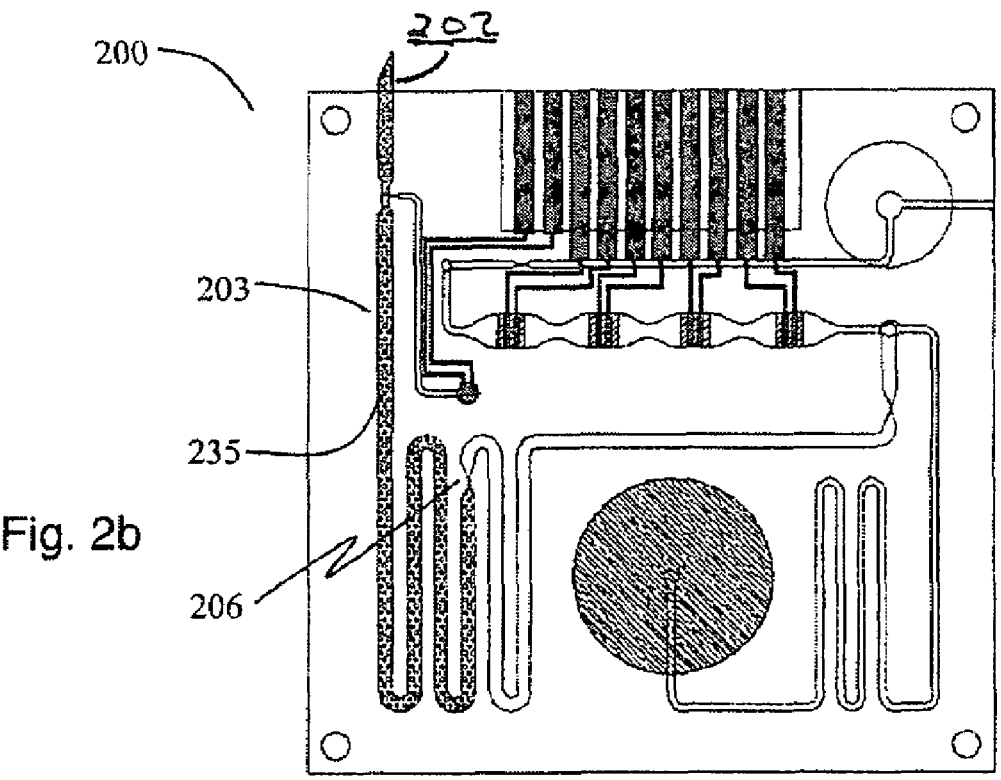

FIG. 2b shows the sampling sequence using the integrated micro-needle 202. The micro-needle is inserted into the desired sampling location, which is a venous sampling source in accordance with an embodiment of the present invention. The slight positive pressure inside the venous system is sufficient to push the blood into the micro-needle 202 and thereafter into the connecting microchannel 203. The sample 235 will flow through the microchannel until it encounters the passive micro-valve 206 in the flow path. Hereafter, a large jump in pressure is required to push the sample beyond this point. In accordance with an embodiment of the present invention, the dimensions of the microchannel 203 and the passive valve 206 are designed such that a pressure of magnitude at least ten times higher than the pressure required for flow in the microchannel is required to push the sample 235 beyond the passive valve 206. The micro-needle is then withdrawn from the sampling source. Owing to the small volumes of the microfluidic system wherein, in accordance with an embodiment of the present invention, the sampled volume is approximately 1 μl, sufficient sample may be collected in approximately 2 to 20 seconds.

Figure 2C:
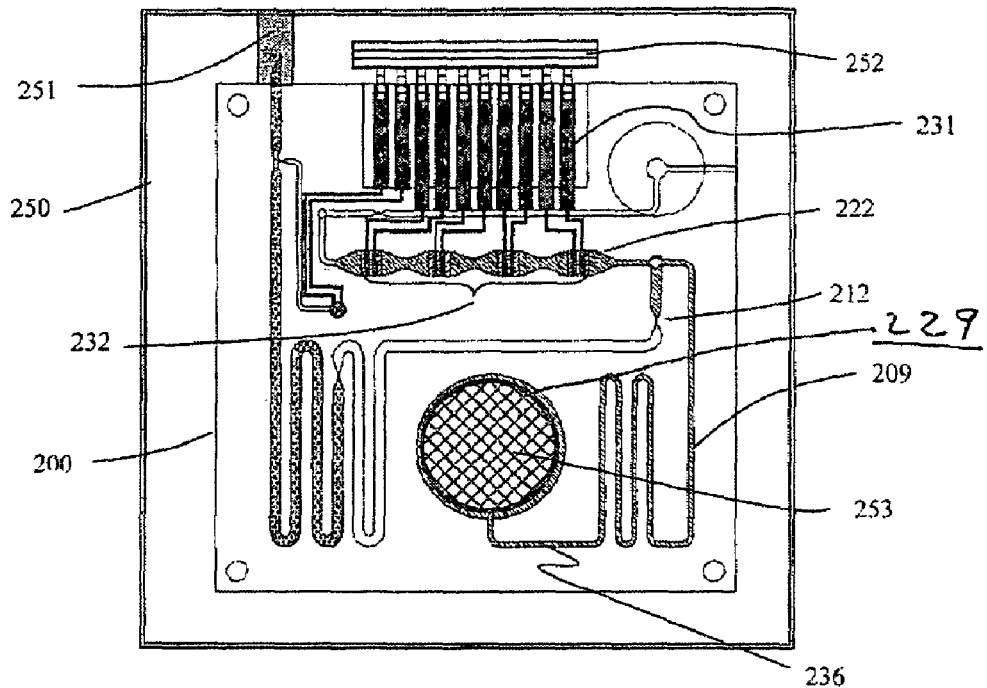

Then the biochip 200 is inserted into a custom-designed socket 250 as shown in FIG. 2c. The socket itself forms a part of the handheld analyzer as described later. This step accomplishes multiple goals, namely: (a) the open end of the microneedle 202 is sealed by a soft plug material 251 contained in the socket 250. Also, an electrical connector 252 makes contact with the electrodes 231 of the sensor array and the on-chip pressure generator. Finally, insertion of the biochip into the socket causes a protrusion 253 on the socket to pressurize and thereby rupture the on-chip calibration solution pouch 229. This releases the calibration solution 236, which flows through the connecting microchannel 209 and enters the detection reservoir 222 wherein it comes in contact with the biosensor array 232. Passive valve 212 ensures that the calibration solution does not backflow towards the sample solution. The calibration solution contains known concentrations of each of the analytes that is to be measured using the biosensor array. The micro-sensors are then calibrated at the given environmental conditions and the response of the biosensors (micro-sensors) at the known concentration is recorded by the analyzer electronics.

Figure 2D:
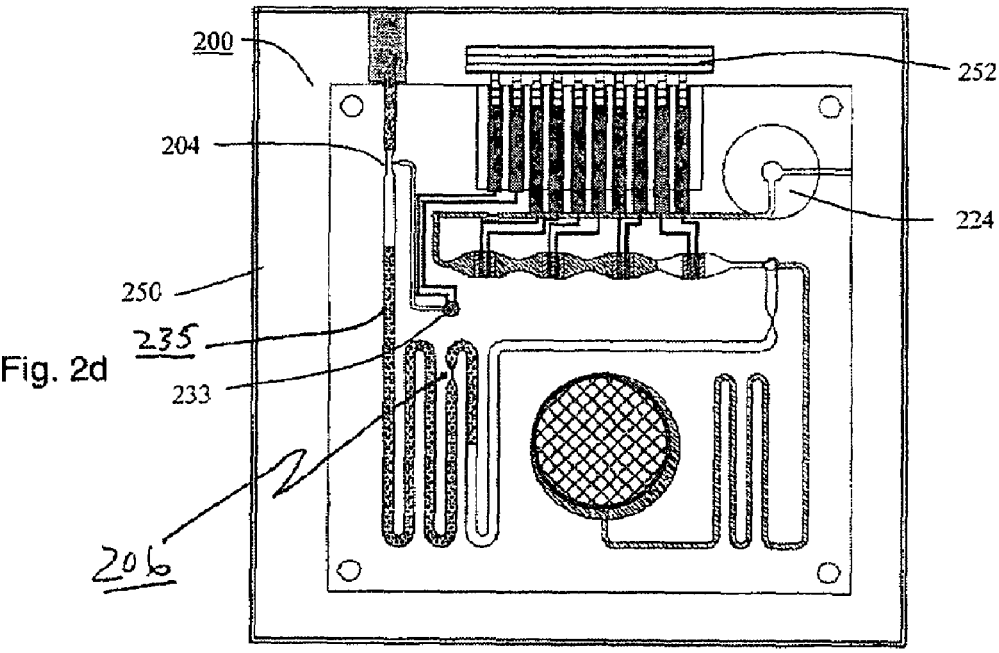

Thereafter, as shown in FIG. 2d, the functional on-chip pressure generator 233 (micro-propulsion system) is actuated by applying a suitable current pulse to the solid-propellant material thereby causing evolution of non-reactive gas. This gas evolution causes a build-up in pressure which splits the sample 235 column at the junction 204 of the liquid channel and the narrow air inlet. The continuing increase in pressure pushes the liquid column beyond the passive valve 206 towards the sensing chamber while simultaneously displacing the calibration buffer solution that occupied the sensing chambers. The calibration buffer is then displaced to the waste reservoir 224.

Figure 2E:
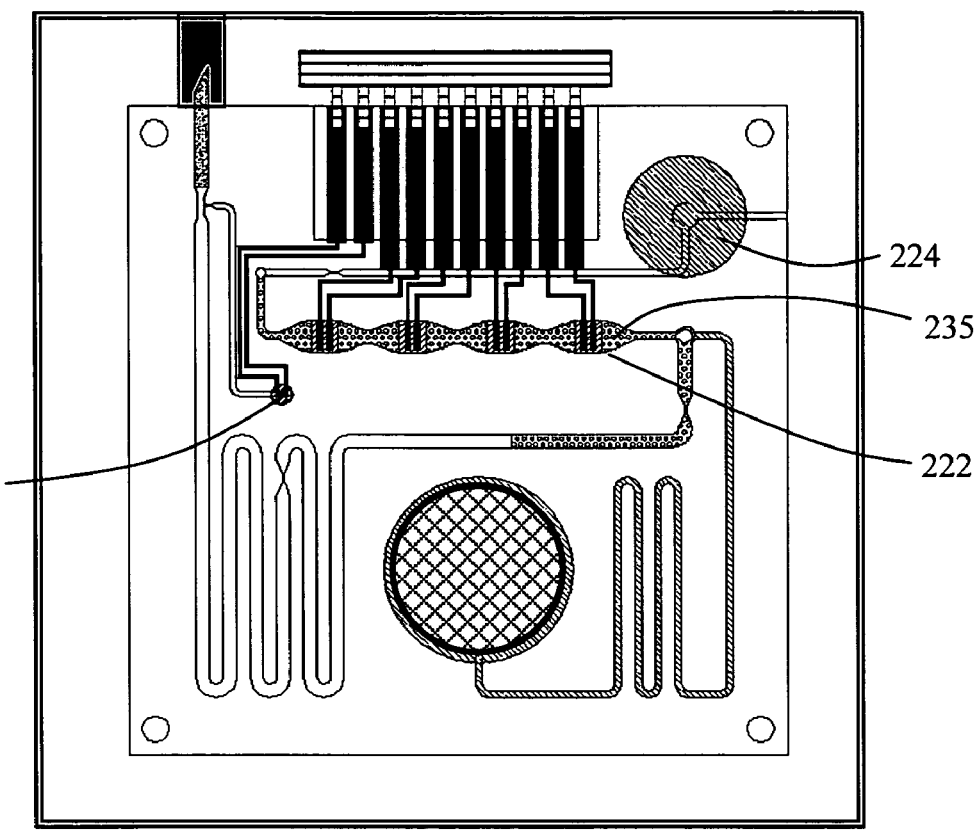

Finally, as shown in FIG. 2e, the sample 235 is delivered to the sensing chamber 222 for measurement of the relevant parameters (e.g., partial oxygen concentration, glucose level, lactate level, pH, hematocrit). The use of the calibration buffer allows for compensation of environmental variables such as variations in temperature. Also, as explained in the operation sequence above, the microfluidic pumping is achieved by (a) insertion of the biochip into the socket and subsequent mechanical displacement of the calibration solution and (b) by applying a brief current pulse to the solid-propellant based functional on-chip pressure generator. Hence, very little power, in fact only during (b) above, is required for microfluidic sequencing thereby making the biochip more suitable for POCT applications wherein limited power can be supplied from a handheld analyzer.

Figure 3A:
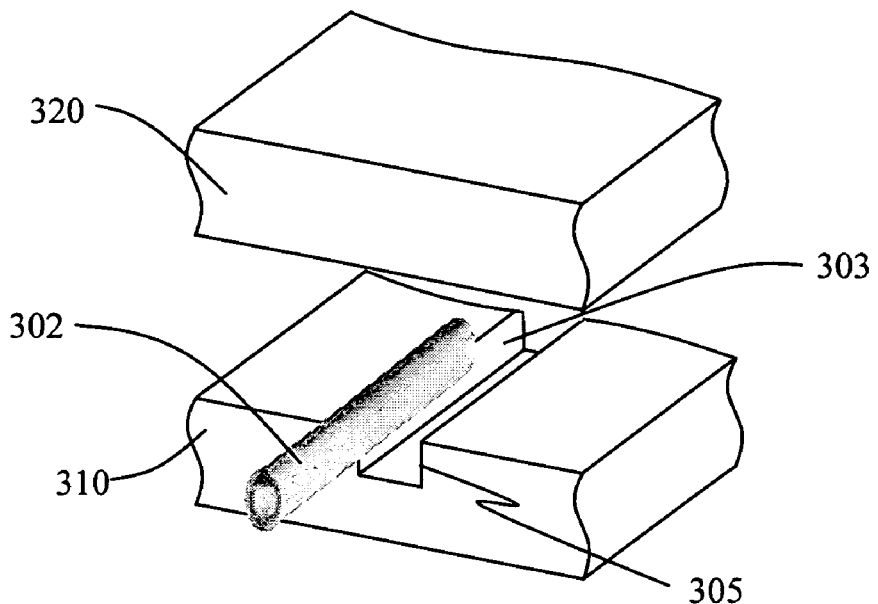
FIGS. 3a-3f show a schematic of the assembly sequence for integrating a metallic microneedle, an SEM image of the substrate, and also the operation of the microneedle with the biochip, in accordance with an embodiment of the present invention.
Figure 3B:
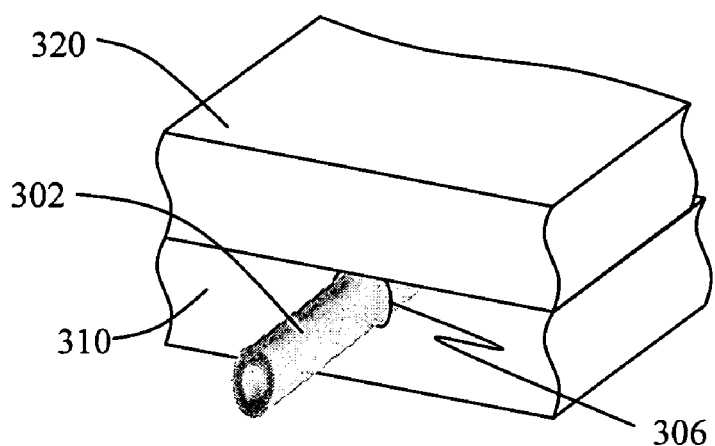
Figure 3C:
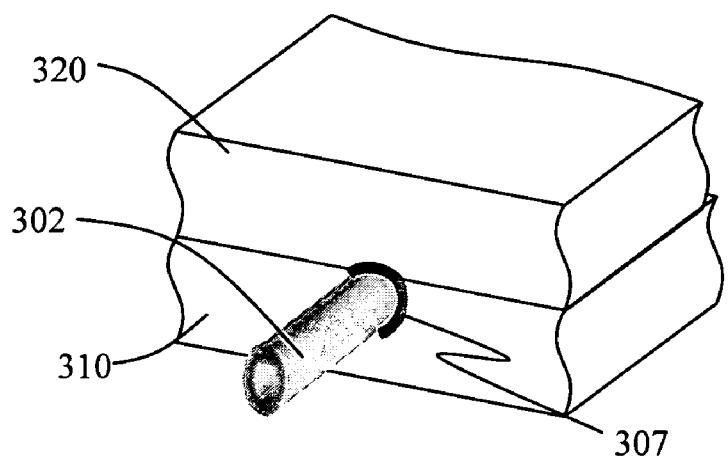

FIG. 3a-3c shows details of the assembly sequence of the micro-needle. The micro-needle 302 is positioned within an appropriately sized microchannel 303 on one of the layers 310. Nominally, the microchannel 303 would have approximately vertical sidewalls 305 at the end of the channel. Then a second, blank substrate 320 is assembled using thermoplastic fusion bonding. In this process, the assembly is heated to beyond the so-called "glass transition region" of the plastic substrate and a high pressure is applied to cause bonding. This also leads to some distortion of the channel sidewalls 306 at the terminal end of the microchannel. Since the micro-needle is composed of a metallic material, it is relatively rigid at the applied pressures and the sidewalls will slightly deform to approximately conform to the shape to the needle. In accordance with an embodiment of the present invention, a 36 gage metallic micro-needle (outer diameter approximately 250 μm, inner diameter 100 μm) is used. As listed previously, the depth of the microchannels is approximately 100 μm, in accordance with an embodiment of the present invention. Hence, it is necessary to increase the depths of these microchannels by suitable micromachining techniques, such as laser micro machining. Thereafter, an epoxy solution 307 is applied at the junction of the micro-needle and the biochip. This ensures that there is no backflow of the sample solution as it is being displaced by the on-chip functional pressure source.

Figure 3D:
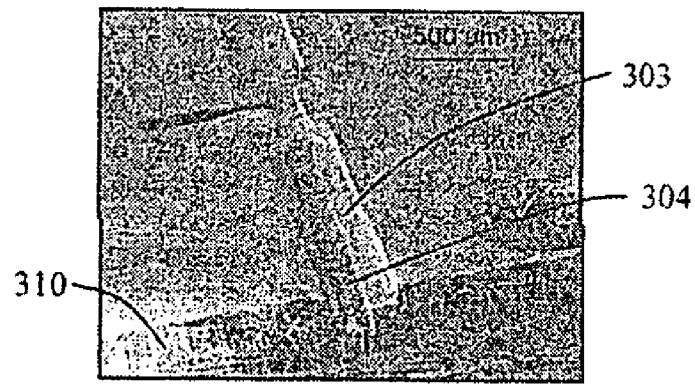
Figure 3E:
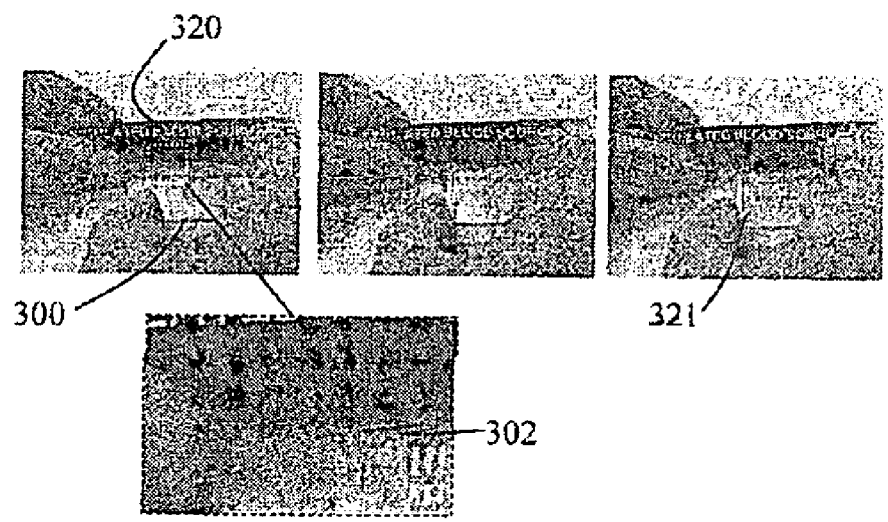

FIG. 3d shows a SEM microphotograph of the microchannel 303 with increased depth 304 achieved by using laser micromachining on a plastic substrate 310. FIG. 3e shows the operation sequence of the biochip with the integrated micro-needle. The pressurized simulated blood source 320 is a flexible reservoir which is filled with dyed DI water, such that a slight excess volume of water is injected into the flexible reservoir to ensure that the liquid is stored under pressure. Thereafter, as shown in the insert of FIG. 3e, the micro-needle is inserted into the simulated blood source and the pressurized liquid fills the microchannel on the biochip via the micro-needle.

Figure 3F:
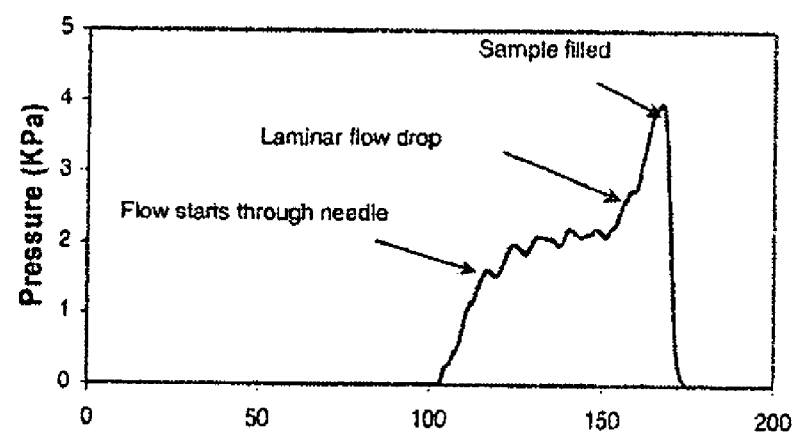

FIG. 3f is a pressure trace recorded at the outlet of the micro-needle showing the distinct pressure jump required to initiate flow through the micro-needle, followed by the slight rise in pressure associated with laminar flow and the subsequent jump in pressure associated with the liquid being locked into position by the passive microvalve.

Figure 4A:
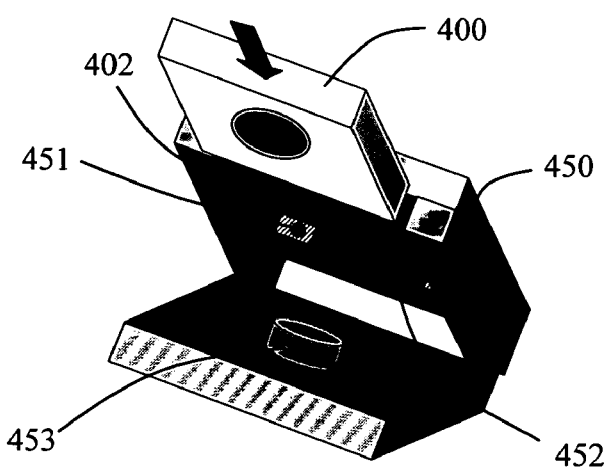
FIGS. 4a-4d show the operation of a custom-designed biochip socket, in accordance with an embodiment of the present invention.

FIGS. 4a-4d show the schematic operation sequence of the custom designed biochip socket, in accordance with an embodiment of the present invention. As shown in FIG. 4a, the socket 450 comprises a bump or a protrusion 453 to break the calibration solution pouch. The dimension, more specifically diameter of this bump is slightly smaller than the diameter of the cavities on layers 2 and 3 of the biochip, which house the calibration solution pouch. Furthermore, the socket 450 also contains an electrical connector 452 and a soft plug 451 composed of a flexible material. The biochip 400 is inserted into the upper half of the socket 450. This action seals the micro-needle inlet 402, and makes contact to the electrical connector 452.

Figure 4B:
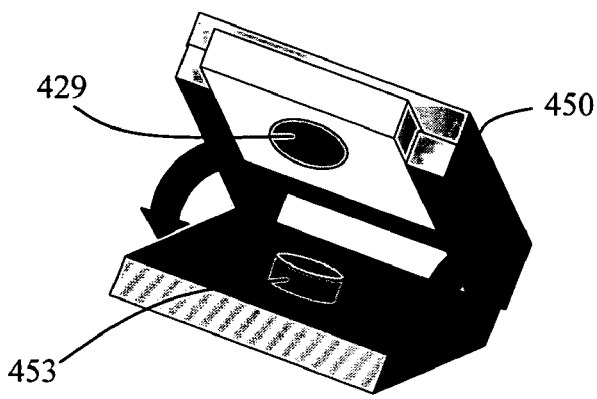
Figure 4C:
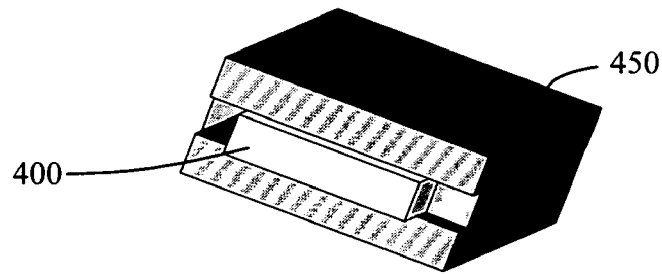
Figure 4D:
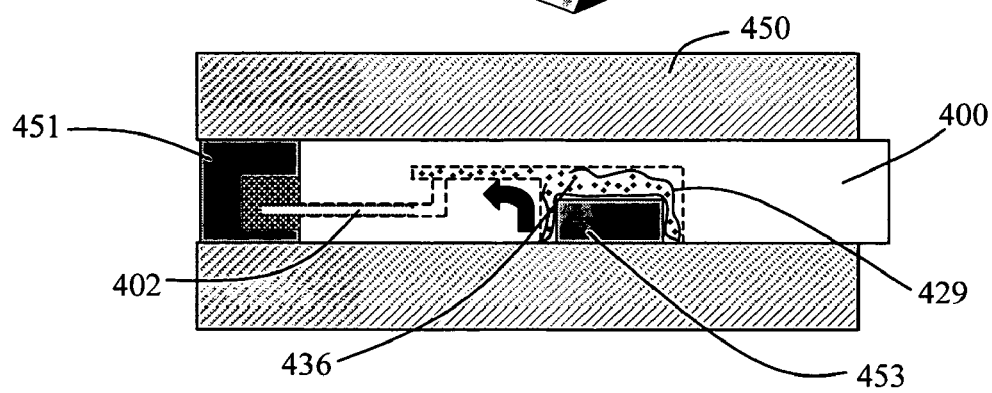

Thereafter, the upper half of the socket is "closed" over the lower half thereby pressing the bump into the calibration pouch 429 as shown in FIGS. 4b and 4c. This causes rupture of the calibration solution pouch 429 and pushes the calibration solution 436 into the microfluidic channels. This sequence of events illustrates the fact that no external power beyond that supplied by the user (by closing the socket) is necessary for displacing the calibration solution. Hence this procedure avoids the use of complex, power-hungry micropumps.

Figure 5A:
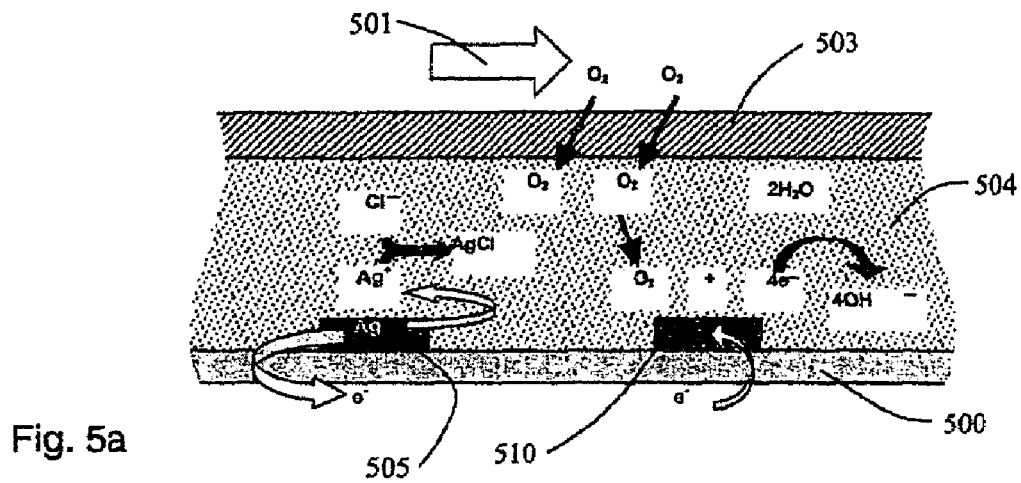
FIGS. 5a-5d show schematic illustrations of an oxygen biosensor operation, a biosensor array and the fabrication process, and also a microphotograph of an actual biosensor array, in accordance with an embodiment of the present invention.

FIG. 5a shows the schematic operation sequence of the basic biosensor namely, the oxygen sensor. The oxygen sensor operates on amperometric principles, as are well known in the art. Essentially the biosensor structure is composed of an anode 510 and a cathode 505 (two electrodes) surrounded by a solid electrolyte membrane 504 (i.e., a solid, gel-based electrolyte solution). The two electrodes may be deposited by evaporating gold film onto a substrate and then electroplating a thin layer of silver onto the gold film, in accordance with an embodiment of the present invention. This arrangement is further ensconced in another membrane 503 which serves as an oxygen semi-permeable layer. When the sample 501 flows over the biosensor, the oxygen molecules from the sample diffuse through the semi-permeable membrane 503 and cause an electrochemical reaction as shown schematically in FIG. 5a. This structure is commonly known as the Clark electrode and is widely known in the art.

Figure 5B:
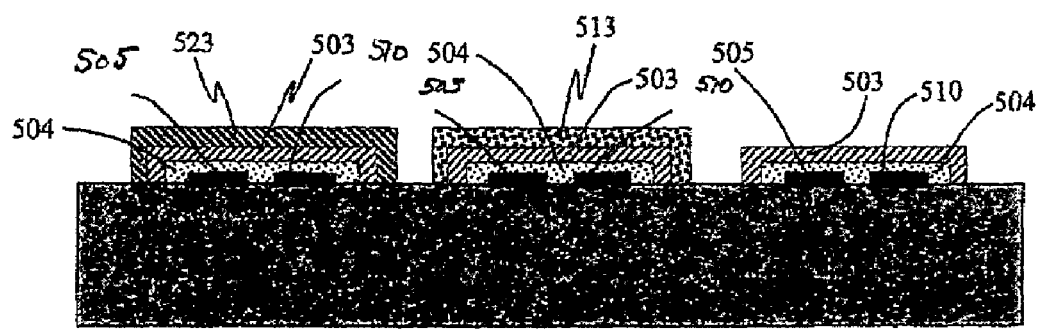

FIG. 5b shows a schematic view of the biosensor array, wherein multiple sensors are fabricated in close proximity to each other such that multiple analytes may be detected simultaneously from the same sample solution. All the biosensors in the array are based on variations in design of the oxygen sensor described above. Specifically each sensor has a two electrode configuration (brought out on conductive traces) with an anode 505, 515, 525 and cathode 510, 520, 530. Each sensor also has the solid electrolyte layer 504 and the oxygen semi-permeable membrane 503. In order to fabricate a Glucose sensor, Glucose Oxidase enzyme is entrapped in a suitable matrix material and deposited as a membrane 513 over the oxygen semi-permeable membrane. A Lactate sensor is fabricated using a similar approach wherein Lactate Oxidase enzyme entrapped in matrix is deposited as a membrane 523 on the basic oxygen sensor. The constructions of these biosensors in not a novel feature of the present invention and the principles and the materials used for these biosensors are widely known in the art. Other sensors such as pH sensors and hematocrit sensors are possible as well, in accordance with various embodiments of the present invention.

Figure 5C:
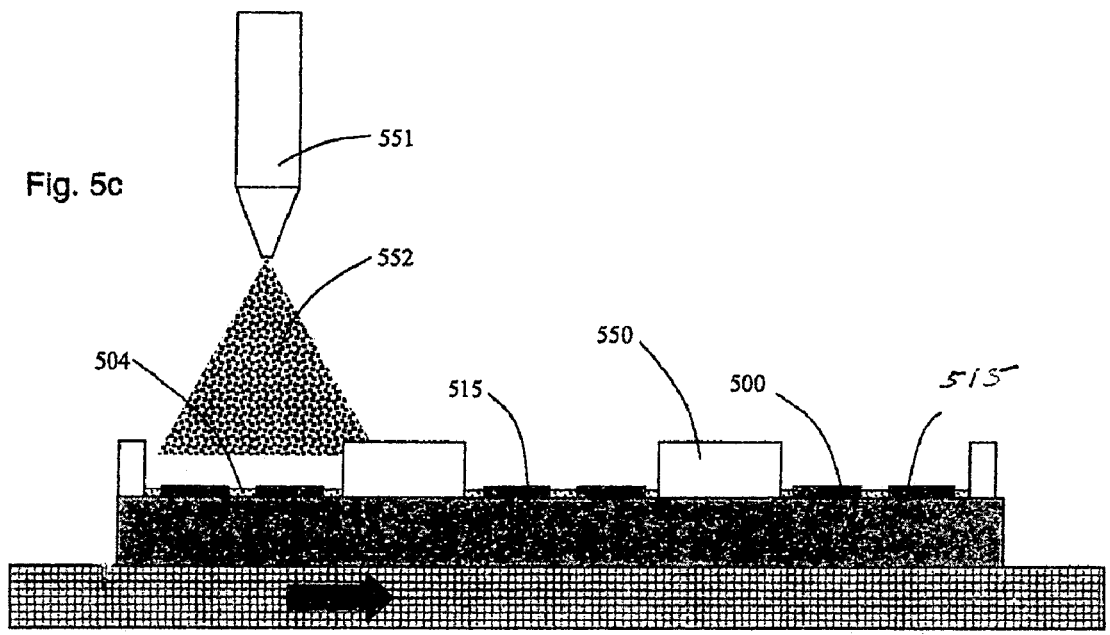
Figure 5D:

FIG. 5c shows a schematic view of a high volume fabrication process for creating the biosensor array, in accordance with an embodiment of the present invention. Conventionally, processes such as spin coating are used for depositing the various membrane materials for microfabricated biosensors. In other examples, as listed previously in U.S. Pat. No. 6,306,594 and U.S. Pat No. 5,837,454, incorporated in its entirety herein by reference, direct deposition of the membrane materials by microdispensing techniques is also used. However, these processes are not scalable for high volume production thereby limiting their application in such cases and also increasing the per device cost. As shown in FIG. 5c, spray coating through a suitable mask layer 550, with the microfabricated electro patterns 515, positioned on a precision X-Y stage which can be moved in precise and minute increments. The membrane material 504 is sprayed 552 through a nozzle 551 which is fixed in position. Since the biochip is covered in parts by the masking layer 550, the membrane material is only deposited in the open regions. By replacing the mask layer for various membrane layers, the desired sensor composition can be achieved in a low cost, high volume manufacturing process. Of course, other commonly accepted processes such as dip-coating or spin-coating may also be used for this application. Furthermore, depending on the deposition technique, the mask layer may or may not be in intimate contact with the substrate. FIG. 5d shows microphotographs of the actual biosensor array.

FIG. 6a shows a block diagram view of the electronics in the handheld analyzer, in accordance with an embodiment of the present invention. FIG. 6b shows a photograph showing the actual handheld analyzer 601 with the biochip socket 605, containing the biochip 600, SMT (surface mount technology) based electronics 608, batteries 606, and display 607. As shown clearly in FIG. 6c, the handheld analyzer is of the size that can comfortably fit in the palm of the operator and the system is well suited towards POCT applications. In accordance with an embodiment of the present invention, the handheld analyzer includes a bio-socket, timing and sequence control circuitry, bio-sensor detection circuitry, a user interface (e.g., control switches), a display, and a power source (e.g., batteries).

Figure 7:
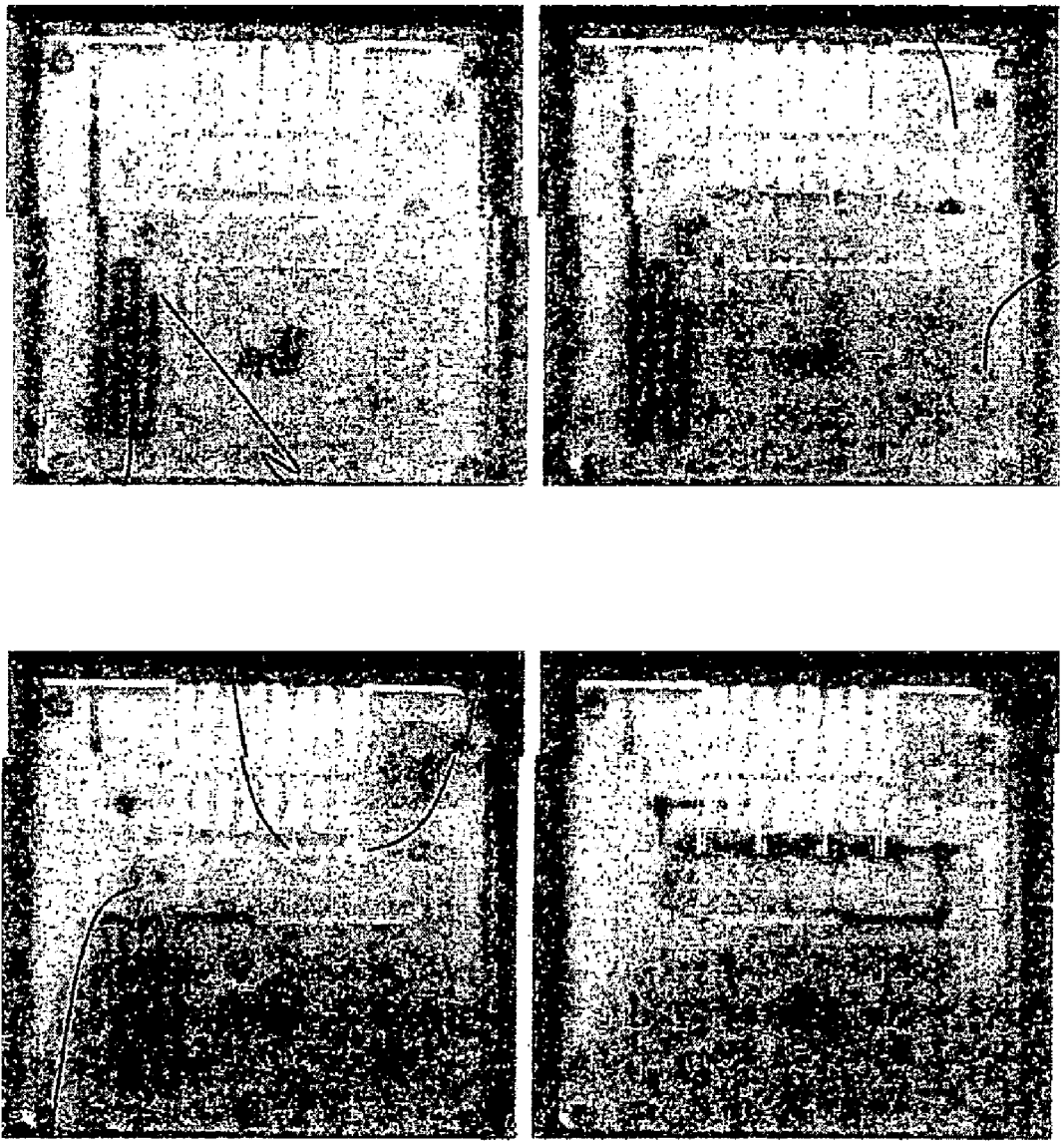
FIG. 7 shows microphotographs of an actual operation sequence of a biochip, in accordance with an embodiment of the present invention.
Figure 8:
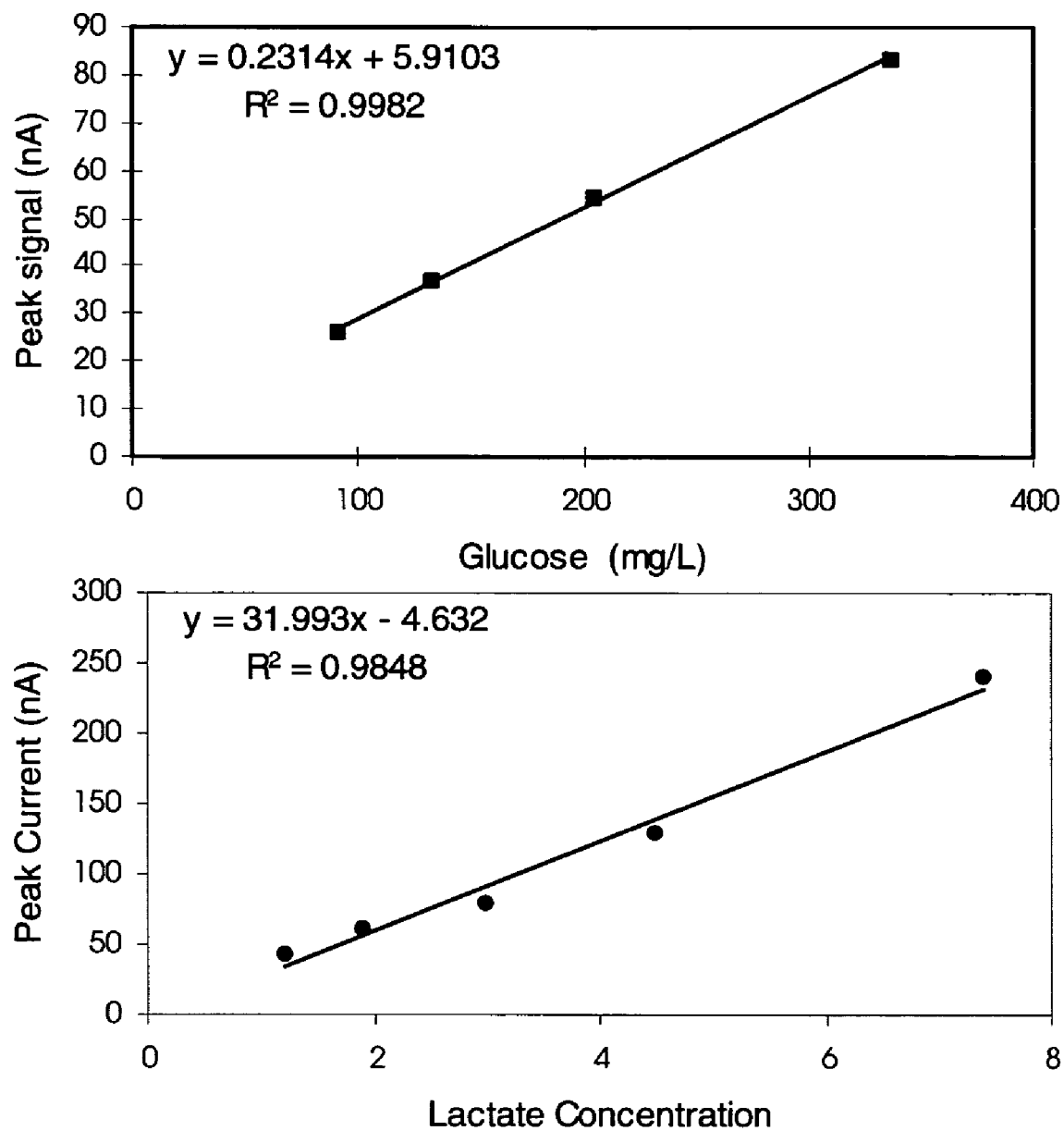
FIG. 8 shows actual measurement results from human blood obtained using a microfabricated sensor array, in accordance with an embodiment of the present invention.

FIG. 7 shows microphotographs showing the actual operation sequence of the disposable biochip clearly illustrating that the desired flow sequence can indeed be achieved on the designed biochip. FIG. 8 shows measurement results for Glucose and Lactate concentrations measured from human blood using the integrated biosensor array.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A disposable, integrated biochip for clinical diagnostic applications, said biochip comprising:
    a. at least one micro-sensor for sensing at least one relevant parameter of said sampled fluid;
    b. micro-calibration system connected to said at least one micro-sensor to calibrate said biochip comprising:
        i. a metallic calibration solution pouch containing a calibration buffer of at least one known concentration of at least one analyte;
        ii. at least one micro-fluidic channel, connecting to said calibration solution pouch, to carry said calibration buffer to said at least one micro-sensor when said calibration solution pouch is ruptured; and
        iii. at least one waste reservoir to accept said calibration buffer after said biochip is calibrated;
    c. a micro-needle for sampling a fluid from a subject; and
    d. a passive micro-fluidic control system, connecting said micro-needle to said at least one micro-sensor, to accept said sampled fluid from said micro-needle and to facilitate movement of said sampled fluid to said at least one micro-sensor.

2. The biochip of claim 1 further comprising a micro-propulsion system connecting to said passive micro-fluidic control system to move said sampled fluid through said passive micro-fluidic control system.

3. The biochip of claim 2 wherein said at least one micro-sensor, said passive micro-fluidic control system, said micro-propulsion system, and said micro-calibration system are collectively fabricated on at least two plastic substrates that are integrated together within said biochip.

4. The biochip of claim 1 wherein said micro-needle is metallic.

5. The biochip of claim 1 wherein said at least one micro-sensor comprises at least one of an electro-chemical oxygen biosensor, an electrochemical glucose biosensor, an electrochemical lactate biosensor, a pH biosensor, and a hematocrit biosensor.

6. The biochip of claim 1 wherein said passive micro-fluidic system comprises: a micro-dispenser reservoir; at least one passive micro-valve; at least one micro-sensor reservoir connecting to said at least one micro-sensor via at least one semi-permeable membrane of said at least one micro-sensor; and at least two micro-fluidic channels connecting together said micro-dispenser reservoir, said at least one passive micro-valve, and said at least one micro-sensor reservoir.

7. The biochip of claim 2 wherein said micro-propulsion system comprises: at least one micro-chamber containing a pressurized gas and being connected to said passive micro-fluidic control system; and at least one micro-heater positioned next to and being in contact with a thermo-plastic membrane of said micro-chamber to release said pressurized gas into an air inlet of said passive micro-fluidic control system upon melting of said thermo-plastic membrane by said micro-heater when an electrical pulse is applied to said micro-heater.

8. The biochip of claim 2 wherein said micro-propulsion system comprises: at least one micro-heater; and at least one solid chemical-propellant positioned on said at least one micro-heater to release an inert gas into an air inlet of said passive micro-fluidic control system upon activation of said at least one solid chemical propellant by said micro-heater when an electrical pulse is applied to said micro-heater.

9. The biochip of claim 3 wherein said at least two plastic substrates comprises at least one of cyclic olefin copolymer, polyimide, polymethylmethaacrylate, PDMS, polyethylene, and polycarbonate.

10. The biochip of claim 5 wherein said oxygen biosensor comprises: a semi-permeable membrane that is permeable to at least oxygen molecules; a solid, gel-based layer of electrolyte solution being in contact with said semi-permeable membrane; and at least two electrodes being in contact with said solid, gel-based layer of electrolyte solution.

11. The biochip of claim 5 wherein said glucose biosensor comprises: a first semi-permeable membrane that is permeable to at least glucose molecules; a glucose oxidase enzyme layer being in contact with said first semi-permeable membrane to oxidize said glucose molecules into at least oxygen molecules; a second semi-permeable membrane being in contact with said glucose oxidase enzyme layer and being permeable to at least said oxygen molecules; a solid, gel-based layer of electrolyte solution being in contact with said second semi-permeable membrane; and at least two electrodes being in contact with said solid, gel-based layer of electrolyte solution.

12. The biochip of claim 5 wherein said lactate biosensor comprises: a first semi-permeable membrane that is permeable to at least lactate molecules; a lactate oxidase enzyme layer being in contact with said first semi-permeable membrane to oxidize said lactate molecules into at least oxygen molecules; a second semi-permeable membrane being in contact with said lactate oxidase enzyme layer and being permeable to at least said oxygen molecules; a solid, gel-based layer of electrolyte solution being in contact with said second semi-permeable membrane; and at least two electrodes being in contact with said solid, gel-based layer of electrolyte solution.

13. The biochip of claim 1 further comprising at least two conductive traces connected to said at least one micro-sensor for monitoring an electric current generated by said micro-sensor.

14. The biochip of claim 1 wherein said at least one relevant parameter comprises at least one of partial oxygen concentration, glucose level, lactate level, pH, and hematocrit.

* * * * *